(12) United States Patent
Matsumoto et al.

(10) Patent No.: US 7,402,150 B2
(45) Date of Patent: Jul. 22, 2008

(54) INJECTION DEVICE

(75) Inventors: Hiroshi Matsumoto, Hyogo (JP);
Masahiro Urakami, Hyogo (JP);
Noriyuki Tanaka, Hyogo (JP);
Yoshitaka Yamashita, Hyogo (JP);
Shinji Kotani, Hyogo (JP); Takashi Hanada, Hyogo (JP); Masafumi Tatsumi, Hyogo (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 0 days.

(21) Appl. No.: 11/515,387

(22) Filed: Sep. 5, 2006

(65) Prior Publication Data

US 2007/0185440 A1    Aug. 9, 2007

(30) Foreign Application Priority Data

Sep. 5, 2005    (JP) ............................. 2005-256403

(51) Int. Cl.
*A61M 37/00* (2006.01)
(52) U.S. Cl. .............................. 604/90; 604/82; 604/89
(58) Field of Classification Search ................... 604/83, 604/84, 85, 88, 89, 90, 92, 181, 187, 188
See application file for complete search history.

(56) References Cited

U.S. PATENT DOCUMENTS

| 2,717,601 | A | * | 9/1955 | Brown ........................ 206/221 |
| 4,561,856 | A | * | 12/1985 | Cochran ...................... 604/143 |
| 4,968,299 | A | | 11/1990 | Ahlstrand |
| 5,226,895 | A | | 7/1993 | Harris |
| 5,380,295 | A | * | 1/1995 | Vacca ......................... 604/187 |
| 5,545,147 | A | | 8/1996 | Harris |
| 6,077,247 | A | | 6/2000 | Marshall et al. |
| 6,319,225 | B1 | * | 11/2001 | Sugita et al. .................. 604/89 |
| 6,406,455 | B1 | * | 6/2002 | Willis et al. ................... 604/68 |
| 6,419,656 | B1 | * | 7/2002 | Vetter et al. ................... 604/90 |
| 6,652,493 | B1 | * | 11/2003 | Das ............................. 604/181 |
| 6,793,646 | B1 | * | 9/2004 | Giambattista et al. ......... 604/90 |
| 6,936,032 | B1 | | 8/2005 | Bush, Jr. et al. |
| 2005/0049550 | A1 | * | 3/2005 | Kirchhofer et al. ............ 604/82 |

FOREIGN PATENT DOCUMENTS

| EP | 0594349 A1 | 4/1994 |
| EP | 0943349 A1 | 9/2000 |
| WO | WO 9748430 A | 12/1997 |
| WO | WO 0062839 A2 | 10/2000 |

* cited by examiner

*Primary Examiner*—Nicholas D. Lucchesi
*Assistant Examiner*—Aarti Bhatia
(74) *Attorney, Agent, or Firm*—Millen, White, Zelano & Branigan, P.C.

(57) ABSTRACT

Disclosed is an injection device for properly dissolving pharmaceutical agents contained in a two-compartment syringe having slidable front and rear walls, and then performing portionwise multiple injections. The injection device comprises a front casing designed to enclose and hold the two-compartment syringe with a double-ended needle attached to the front end of it, a rear casing designed to receive the thus held two-compartment syringe being inserted in the rear-end first manner, and to lock and hold the front casing, a piston rod placed in the rear casing and designed to push from behind and carry forward the slidable rear wall, wherein the piston rod can be pushed forwardly from behind the rear casing, and a spring provided so that, when the front end of the piston rod is moved backward, the spring may be once compressed and then push the piston rod to a forward position again, and forwardly drives the slidable rear wall to abut on the slidable front wall.

10 Claims, 6 Drawing Sheets

INJECTION DEVICE

FIELD OF THE INVENTION

The present invention relates to an injection device, in particular to an injection device in which a two-compartment syringe containing pharmaceutical agents separately from each other is loaded, and which injection device conducts mixing of the pharmaceutical agents before injection.

BACKGROUND OF THE INVENTION

To maintain their stability, injectable preparations of a peptide, e.g., growth hormone, are provided in two-component forms consisting of a dried pharmaceutical component prepared by lyophilization, for example, and a liquid pharmaceutical component (a solvent liquid such as a buffered solution) in which the former component is dissolved to give an injectable liquid. And, to allow easy and reliable handling by patients, two-compartment syringes (also called dual-chamber cylinder ampoules) are widely employed for, e.g., human growth hormone preparations, in which those two components are contained in a single syringe separately from each other (see FIG. 1).

A two-compartment syringe, as shown in FIG. 1 as a side cross-sectional view, leftward direction of which represents the upward direction, is partitioned in its interior with two slidable walls in a liquid tight fashion (slidable front wall 2 and slidable rear wall 3) to enclose a front space 4 and a rear space 5. In the front space 4 and slightly forward of the slidable front wall 2, an elongated longitudinal groove 6 is defined in the inner wall of the two-compartment syringe, which groove has a length enough to stride the thickness of the slidable front wall 2 (therefore being a little longer than the thickness of the slidable front wall 2), so that a bypass through the groove may be created when the whole body of the slidable front wall 2 is placed within the range of the groove 6. In the front space 4 is enclosed a dried pharmaceutical component 10 such as a lyophilized powder, and in the rear space 5 a solvent liquid 11 used to dissolve the dried pharmaceutical component. At the front end of the two-compartment syringe 1, a septum 13 which can be pierced by a double-ended needle is fit in a fluid tight fashion and secured there with a cap 15 from outside.

Mixing of the dried pharmaceutical component 10 and the solvent liquid 11 is performed within the two-compartment syringe as follows: referring to FIG. 2, the syringe is held with its front end facing upward, and then a double-ended needle 18 is fixed as shown piercing through the septum 13 at the front end. The lumen of the double-ended needle thus communicates the front space 4 with the outside of the syringe. Then, the head 21 of the piston rod 20 of the injection device is put on the back of the slidable rear wall 3. As the piston rod 20 is pushed in, the liquid pharmaceutical component in the rear space 5 (and also air if present) and the slidable front wall 2 also are pushed in together with the slidable rear wall 3. Referring to FIG. 3, when rear end of the groove 6 is exposed at the rear edge of the slidable front wall 2, a bypass is formed through the groove 6 between the front space 4 and the rear space 5, through which bypass the solvent liquid 11 contained in the rear space 5 begins to be transferred into the front space 4, whereas the slidable front wall 2 comes to a halt there. When the piston rod 20 is further pushed in until the slidable rear wall 3 comes to abut on the slidable front wall 2, all the solvent liquid 11 in the rear space 5 has now been transferred into the front space 4 and mixes there with the pharmaceutical component 10 and dissolves it to form an injectable liquid 25 (FIG. 4). After the injectable liquid 25 is constituted, the piston rod 20 is further pushed in and the slidable rear wall 3 and the slidable front wall 2 together are thus moved forward so that the air in the front space 4 is expelled through the double-ended needle 18 thus to make the syringe ready for injection (FIG. 5).

In the case of a peptide hormone preparation such as growth hormone, a long-term, regular and portionwise repeated administration is needed. Such administration is conducted by a patient himself or some member of the patient's family (hereinafter referred collectively to as "patients"). The patients receive two-compartment syringes containing undissolved pharmaceutical components together with an injection device in which one of such syringes is to be loaded (see patent document 1 and FIGS. 6 and 7), and they by themselves perform the processes of mixing of the pharmaceutical components to dissolve within the two-compartment syringe and injection of the injectable liquid thus formed. FIG. 6 shows one such injection device before the dissolving process and FIG. 7 after dissolution is completed (leftward direction in both drawings represents the upward direction). Referring to FIGS. 6 and 7, mixing of the pharmaceutical components in the two-compartment syringe is performed by inserting the two-compartment syringe, held by a front casing 31' of the injection device, into the front end of a rear casing 32' of the injection device. This process of mixing and dissolution is just simple and can be done by patients without difficulty.

However, cases were reported at a certain frequency in which unexpected leak of liquid occurred from two-compartment syringes with an attached double-ended needle, during the mixing and dissolving processes done at patients' homes. Through various trials, the present inventors revealed that this leak of liquid was occurring in the following manner. That is, when the slidable rear wall 3 was forcefully and abruptly pushed in by patients, the forward transfer of the solvent liquid through the groove 6, as shown in FIG. 3, couldn't keep pace with it and thereby the slidable front wall 2 is pushed in beyond the groove 6 and urged in front of it, with the solvent liquid remaining between the slidable frond wall 2 and the slidable rare wall 3 (FIG. 8). Then, as the piston rod is further pressed in by patients, with part of the solvent liquid enclosed between the slidable front and rear walls 2 and 3, these walls advance together with the solvent liquid enclosed between them and, when the slidable rear wall 3 comes entirely within the range of the groove 6, the solvent liquid leaks backward through the groove 6 (FIG. 9), which is now in communication with the outside of the syringe.

When such leak of liquid as above has occurred, the pharmaceutical components are not properly mixed, and thus not only the volume of the liquid that can be ejected but also the concentration of ingredients in that liquid have been deviated from a predetermined specification, thereby rendering the two-compartment syringe improper for further use. It was also revealed that as patients became accustomed to the handling of the injection device, such rough handling of the device, on the contrary, would get more likely to take place. Thus it was difficult to eradicate occurrence of such troubles as above by simply calling their attention to the manner in which they use the device.

On the other hand, a type of device is known which utilizes a screw-based mechanism for pushing in the piston for dissolving the pharmaceutical components in the two-compartment syringe (see Patent Document 2). However, it is inconvenient and not preferable considering the diversity of patients that, in the process of dissolving, patient have to turn a screw by hand in order to push in the piston rod, because it makes handling of the device somewhat complex and thus requires more time in the dissolving process.

An injection device has been reported in which dissolving and injection of the ingredients in a two-ingredient capsule is performed using a spring (see Patent Document 3). This injection device works as follows. The ingredients are mixed when a plunger which is placed at the rear end of the loaded two-ingredient capsule is moved forwardly by the force of a spring provided in the device. Then, activation of a trigger releases the fixed capsule and allows it to be urged forwardly by the spring, causing a double-ended needle to pierce a membrane placed at the forward end of the capsule and to let the needle project from the device and eject the injectable liquid. With this device, only a single administration is possible, for the spring, once used, gets relaxed from its compressed state, and all the ingredients has been injected at once, without having provided any means for stepwise halt of the process of injection. Expulsion of air from the capsule prior to injection of the ingredient is also impossible with this device, since it, after dissolving the ingredients in the capsule, allows only a single step of operation, i.e., injection of all what is contained in the capsule.

[Patent Document 1] Japanese Patent Application Publication No. H11-267205
[Patent Document 2] Japanese Patent Publication No. H6-61361
[Patent Document 3] WO 97/48430

SUMMARY OF THE INVENTION

Upon the above background, the objective of the present invention is to provide an injection device, which is easy to handle and simple in structure, to be used for dissolving the pharmaceutical components contained in a two-compartment syringe loaded in it and then performing portionwise multiple injections, wherein the slidable rear wall is prevented from being abruptly pushed in when dissolving the pharmaceutical components, thereby guaranteeing proper mixing.

As a result of repeated studies to accomplish the above objective, the present inventors unexpectedly found that the problem of leak of liquid can be resolved, and thereby proper mixing and dissolution of the pharmaceutical components guaranteed, while enabling portionwise multiple injections. This can be done, according to the finding, by (i) providing in a injection device a piston rod that is backwardly slidable and supported at a forward position by a spring, so that, when a two-compartment syringe is loaded in the injection device and the piston rod thus once pushed back by the slidable rear wall of the two-compartment syringe while compressing the spring, the piston rod may then forwardly advance utilizing the repulsive force of the spring and push in the slidable rear wall, as needed for mixing the pharmaceutical components, and (ii) also allowing the piston rod to be manipulated from outside for further pushing in of the slidable rear wall. The present invention was completed based on the finding and further studies.

Thus, the present invention provides what follows:

1. An injection device for receiving a two-compartment syringe having a front end equipped with a septum that can be pierced by a double-ended needle, a cylindrical side wall, a slidable front wall and a slidable rear wall that are liquid-tightly and slidably fitted in the side wall, and a bypass which is defined in the internal surface of the side wall between the front end and the slidable front wall and has a longitudinal length sufficient to stride the thickness of the slidable front wall, the two-compartment syringe containing a first pharmaceutical component in the front space defined between the front end and the slidable front wall and a second, liquid pharmaceutical component in the rear space defined between the slidable front wall and the slidable rear wall; mixing, in the two-compartment syringe, the first pharmaceutical component and the second pharmaceutical component; and then conducting injection of thus prepared injectable liquid, the injection device comprising a front casing designed to enclose and hold the two-compartment syringe with a double-ended needle attached to the front end of the two-compartment syringe, a rear casing designed to receive the two-compartment syringe held by the front casing being inserted in a rear-end first manner, and to lock and hold the front casing, with the two-compartment syringe inserted in the rear casing, a piston rod placed slidably in the longitudinal direction in the rear casing and designed to push from behind and carry forward the slidable rear wall, wherein the piston rod can be pushed forwardly from behind the rear casing, and a spring provided in association with the piston rod in the region between the front end of the piston rod and rear part of the rear casing so that, when the front end of the piston rod is moved backward, the spring may be compressed and then push the piston rod to a forward position again, wherein the spring has sufficient length and strength such that, when the two-compartment syringe held by the front casing is inserted in the rear casing and the front casing is locked by the rear casing, with the septum pierced by a double-ended needle to put the front space into communication with the outside, the spring is once compressed, by the piston rod being moved backward due to the pressure applied by the slidable rear wall of the two-compartment syringe, and then, by its repulsive force, forwardly drives the slidable rear wall together with the second pharmaceutical component and the slidable front wall, and, after the rear end of the bypass is exposed behind the slidable front wall, push in the slidable rear wall until it abuts on the slidable front wall, thereby transferring the second pharmaceutical component into the front space.

2. The injection device as defined in (1) above further comprising a one-way stopper means which, at a position forward of the position where the piston rod rests (on the spring in its natural length) before insertion of the two-compartment syringe, allows the piston rod to be pressed in and advanced but prevents the piston rod from being moved backward.

3. The injection device as defined in (2) above, wherein the one-way stopper means comprises a rack formed on the piston rod and a one-way stopper tooth that is formed in the rear casing and engages the rack to prevent backward movement of the rack.

4. The injection device as defined in (3) above, wherein the rack is formed on the piston rod in the rear of the position of the piston rod that comes opposite to the one-way stopper tooth when the piston rod is supported, before the insertion of the two-compartment syringe, by the spring at the natural length thereof.

5. The injection device as defined in (4) above, wherein the piston rod is in mutually unrotatable engagement with the rear casing, wherein behind the rear casing is provided, in a rotatable fashion relative to the rear casing, an ejection volume controller member having a female screw through which the piston rod runs, and wherein, on the outer surface of the piston rod, a male screw is formed which engages the female screw.

6. The injection device as defined in (5) above, wherein the piston rod and the rear casing are made mutually unrotatable by having non-circular cross sections that engage with each other.

7. The injection device as defined in (6) above, wherein the piston rod and the rear casing is made mutually unrotatable through engagement of the piston rod and the one-way stopper tooth of the rear casing.

8. The injection device as defined in one of (5) to (7) above, wherein the male screw is a partial screw formed so as to sandwich the rack from both sides thereof.

9. The injection device as defined in (8) above, wherein the threads of the male screw on both sides of the rack project higher than the top of the teeth of the rack.

According to the present invention as defined above, such a concern is eliminated that the slidable rear wall be abruptly pushed in when the pharmaceutical components are mixed by inserting the two-compartment syringe into the rear casing of the injection device, even if the two-compartment syringe is abruptly inserted, for the spring once moves backward and then, making use of the repulsive force thus created in the spring, pushes in the slidable rear wall. The slidable rear wall, therefore, is prevented from being abruptly pushed in, and proper, automatic mixing of the pharmaceutical components is thus guaranteed. Further, as a piston rod is provided in such a manner that allows its operation from outside, portionwise multiple injections are now available after automatic mixing of the pharmaceutical components within the two-compartment syringe. Also, according to the present invention, such an injection device for a two-compartment syringe is realized that is of a simple structure, using relatively low-cost materials. Accordingly, it is possible to provide a disposable type, low-cost injection device which is to be discarded when all the injectable liquid in the two-compartment syringe has been used for injection.

Figure 1:
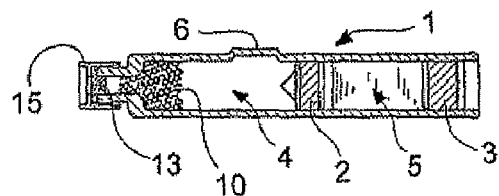
FIG. 1 is a schematic side view of a two-compartment syringe.
Figure 2:
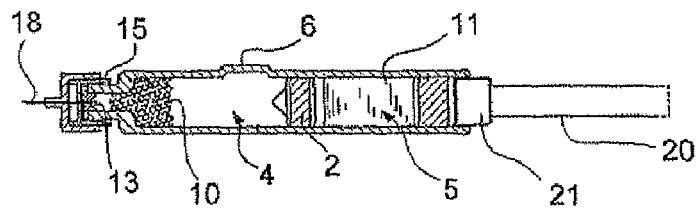
FIG. 2 is a schematic side view of a two-compartment syringe illustrating the staring step of a mixing procedure.
Figure 3:
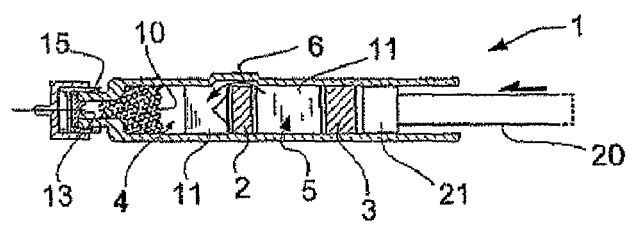
FIG. 3 is a schematic side view of a two-compartment syringe at the step of transferring a solvent liquid through a bypass.
Figure 4:
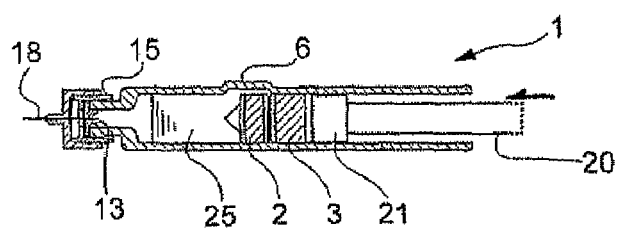
FIG. 4 is a schematic side view of a two-compartment syringe in which the transfer of the solvent liquid has been completed.
Figure 5:
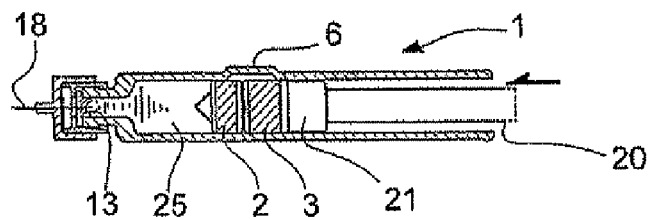
FIG. 5 is a schematic side view of a two-compartment syringe which is ready for injection.
Figure 6:
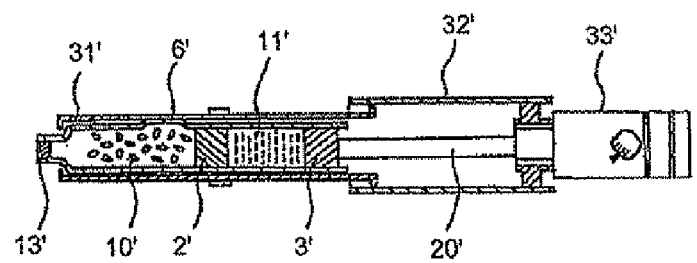
FIG. 6 is a side cross sectional view illustrating an example of prior-art injection devices prior to mixing of the pharmaceutical agents in the two-compartment syringe.
Figure 7:
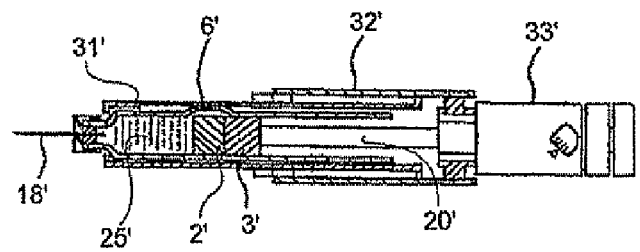
FIG. 7 is a side cross sectional view illustrating an example of prior-art injection devices after mixing of the pharmaceutical agents in the two-compartment syringe.
Figure 8:
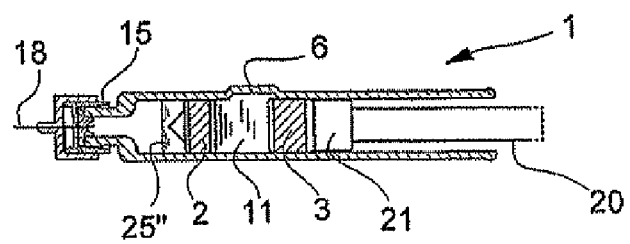
FIG. 8 is a schematic side view illustrating a failed process of mixing the pharmaceutical agents in a two-compartment syringe.
Figure 9:
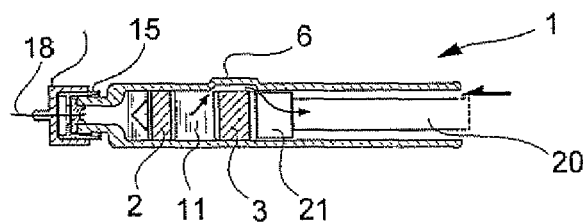
FIG. 9 is a schematic side view illustrating leak of liquid following a failed process of mixing the pharmaceutical agents in a two-compartment syringe.

1=two-compartment syringe
2, 2'=slidable front wall
3, 3'=slidable rear wall
4=front space
5=rear space
6, 6'=groove (bypass)
10, 10'=dried pharmaceutical agent
11, 11'=solvent liquid
13, 13'=septum
15=cap
18, 18'=double-ended needle
20=piston rod
21=head of the piston rod
25, 25', 25"=injectable liquid
31, 31'=front casing
32, 32'=rear casing
33, 33'=ejection volume controller member
34=projection
35=piston rod
35h=head of the piston rod
36=coil spring
38=groove
40=one-way stopper tooth
42=rack
44=groove
50=female screw
52=male screw
55=sleeve
57=scale mark
59, 59'=fin
61=notch
62=projection 63=projection
64=longitudinal groove
65=opening
66=cylindrical portion
67=inner surface
69=U-shaped slit
70=cantilever

DETAILED DESCRIPTION OF THE INVENTION

As two-compartment syringes are well known and multiple products are on the market, one of them may be chosen in accordance with the volume of injectable liquid to be mixed and prepared, and dimensions of the injection device maybe adjusted to it.

There are no specific limitations as to the form of the front casing insofar as it can enclose and hold the two-compartment syringe with a double-ended needle attached to the front end of it. There are also no specific limitations as to the form of the rear casing insofar as it can receive the two-compartment syringe which is held by the front casing and inserted in the rear-end first manner, and lock and hold the front casing, with the two-compartment syringe inserted in the rear casing. Any means as desired may be used for locking the front casing and the rear casing, with at least rear part of the two-compartment syringe is enclosed, and any suitable means may be selected as desired according to a given general structure of the front casing and the rear casing. An example of such means is a combination of a projection and a recess or a face of a step provided at corresponding positions so that they engage when the front casing and the rear casing are positioned to fit each other. An example of such a projection is a resiliently supported projection so as to snap-fit in a corresponding recess. A simple way to resiliently support a projection provided in the wall of the front or rear casing in such a manner is to support the projection by a cantilever consisting of a part of the casing wall defined by a cut, e.g. a U-shaped cut, made around the projection, in the wall supporting the projection. It is preferable that a pair of such projections are provided, e.g., symmetrically on both side in the front (or rear) casing. In the case where both casings are locked by bringing a side face of a projection into engagement with a face of a step formed in the wall of the rear (or front) casing, a path (e.g., a groove) leading to the face of a step may be made in the wall of the rear (or front) casing for allowing the projection formed in the front (or rear) casing to pass through when the two-compartment syringe held by the front casing is inserted into the rear casing.

Any specific form may be given as desired to the piston rod, which is placed slidably in the longitudinal direction in the rear casing for pushing from behind the slidable rear wall to advance, insofar as it can be pushed forwardly from behind the rear casing. The piston rod may, for example, be thrusting with its rear part from the rear end of the rear casing, or it may be placed within the rear casing and be pushed forwardly by a separate member extending from behind the rear casing into the rear casing.

The spring provided in association with the piston rod is preferably a coil spring put around the piston rod within the rear casing. In this case, the rear end of the coil spring may be supported by, e.g., the inner surface of the rear casing around the piston rod. Transmission of force between the coil spring and the piston rod may be made by providing, in a part of the piston rod (e.g., somewhere near its head), a projection projecting beyond the inner diameter of the front end of the coil spring, or by giving the head of the piston rod a greater diameter than the inner diameter of the coil spring.

The length and strength of the spring attached around the piston rod may be determined so that they are sufficient to push the slidable rear wall and make it abut on the slidable front wall of the two-compartment syringe by the repulsive force created by temporary retraction and compression of the spring which is pushed, via the head of the piston rod, by the slidable rear wall of the two-compartment syringe, when the two-compartment syringe held by the front casing is inserted into the rear casing. Proper ranges of the length and strength of the spring can be readily calculated based on the position at which the slidable rear wall is to abut on the slidable front wall within the two-compartment syringe inserted in the injection device, and the amount of force necessary for making the slidable rear wall abut on the slidable front wall at the very position. With the front space being in communication via the bypass with the rear space, and the slidable rear wall being not in contact with the slidable front wall, the spring is only required to advance the single slidable rear wall alone against the frictional force between it and the inner surface of the two-compartment syringe. After the slidable rear wall abuts on the slidable front wall, however, the fictional force between the two slidable walls and the inner surface of the two-compartment syringe resists the repulsive force left in the spring for any further advancement of the slidable rear wall. Therefore, the strength of the spring is determined so as not to advance the both slidable walls in a body from the position. Meanwhile, at the stage before the front space comes into communication with the rear space, though the advancement of the slidable rear wall involves that of the slidable front wall, the spring is capable of pressing the slidable rear wall with a sufficient strength of force to push in the both slidable walls, for the spring, in this stage, is in more compressed state.

According to the above configuration, by inserting the two-compartment syringe, with an attached double-ended needle and being held by the front casing, into the rear casing and then locking the front casing to the rear casing, the slidable rear wall of the two-compartment syringe is advanced by the repulsive force of the spring that is temporarily compressed, until it abuts on the slidable front wall. In this step, as any abrupt advancement of the slidable rear wall is prevented due to the frictional force between the slidable rear wall (or also the slidable front wall) and the inner surface of the two-compartment syringe, a proper mixing process of the pharmaceutical agents in the two-compartment syringe is performed without fail.

The injection device of the present invention, more preferably, is further provided with a one-way stopper means which, at a position forward of the position where the piston rod rests, before insertion of the two-compartment syringe, being supported by the spring at its natural length, allows the piston rod to be pressed in and advance but prevents backward movement of the piston rod. Any specific from may be given as desired to such a one-way stopper means and it may thus be designed as deemed proper. A typical but non-limiting example is a combination of a rack formed on the piston rod and at least one one-way stopper tooth that engages the rack. When such a combination of a rack and a one-way stopper tooth is employed, the rack is formed on the piston rod in the rear of the position on the piston rod that comes opposite to the one-way stopper tooth when the piston rod is supported, before the insertion of the two-compartment syringe, by the spring at its natural length. By this configuration, while backward movement of the piston rod and compression of the spring are allowed during insertion of the two-compartment syringe, the piston rod becomes unable be moved backward when the spring has returned to mix the pharmaceutical agents in the two-compartment syringe and is further pressed in until the expulsion of air is completed, thereby preventing air from being drawn into the syringe through the needle, for the slidable front and rear walls are unable to move backward any more. There are no specific limitations as to the form of the teeth of the rack and the one-way stopper tooth insofar as they are so configured that the tip of the one-way stopper tooth engages the rack and blocks its movement when the rack is about to be moved backward, but that advancement of the rack is allowed when it is pushed forward. A proper cross sectional shape of each tooth of the rack includes a relatively steep rear face and a front face with a relatively gently slope. A proper example of a one-way stopper tooth is one that has a generally forwardly slanted cross section.

In the present invention, more preferably, the piston rod is in mutually unrotatable engagement with the rear casing, a male screw is formed on the outer surface of the piston rod, and, behind the rear casing, an ejection volume controller member having a female screw engaging that male screw is provided in a rotatable fashion relative to the rear casing. Prior to its rotation, the ejection volume controller member is placed abutting on the rear casing. From the position, a gap of a predetermined distance may be created between the rear casing and the ejection volume controller member, by rotating the ejection volume controller member by a predetermined angle in the direction opposite to the winding direction of the helix of the male screw's threads formed on the piston rod, thereby moving the ejection volume controller member backward by the predetermined distance which corresponds to the pitch of the male screw and the angle of rotation. Then, by forwardly pressing the ejection volume controller member to advance until it abuts on the rear casing, the piston rod is advanced by that predetermined distance, thereby ejecting through the needle a predetermined amount of the injectable liquid contained in the two-compartment syringe.

To make the piston rod and the rear casing mutually unrotatable, for example, at least part of the piston rod is formed to have a non-circular cross section, and, within the range of the longitudinal movement of the piston rod, the rear casing is provided with a portion having a non-circular cross section to engage that part. The location where to place such a portion may be chosen as desired. A preferable example is one that makes use of the engagement of a one-way stopper tooth with the piston rod. In this case, a broad one-way stopper tooth, for example, may be employed for engagement with a piston rod (and rack formed on it) of a corresponding width. Or the piston rod may be given a longitudinal groove which the one-way stopper tooth engages and passes through, within which groove a rack also may be formed for engagement.

In the case where, along the length of the piston rod, the range where the rack is formed overlaps the range where a male screw is formed, the male screw may be formed as comprising partial screws sandwiching the rack portion of the piston rod, because it is not necessary for a male screw to have an uninterrupted thread. In such a case, the male screw may be formed simply on the side face of the rack. However, it is more preferable that the male screw is formed so that it's threads project higher than the top of the teeth of the rack on both sides of the rack, for it will add to the effect to prevent the rotation of the piston rod, since the one-way stopper tooth engaging the rack comes to be supported by being sandwiched between the pair of partial screws.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding Japanese Application No. 2005-256403, filed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

EXAMPLES

While the present invention will be described in further detail below with reference to typical examples, it is not intended that the present invention be limited to the examples.

Figure 10:
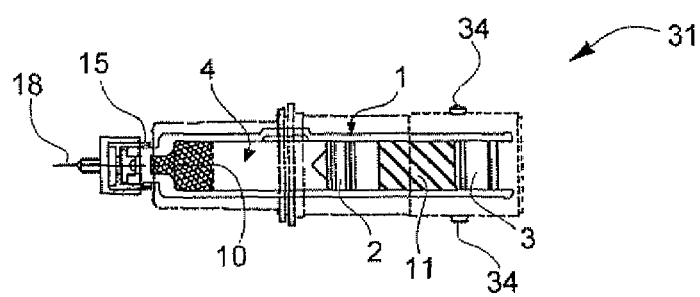
FIG. 10 is a side cross sectional view of the front casing of the injection device holding a two-compartment syringe with an attached double-ended needle.
Figure 11:
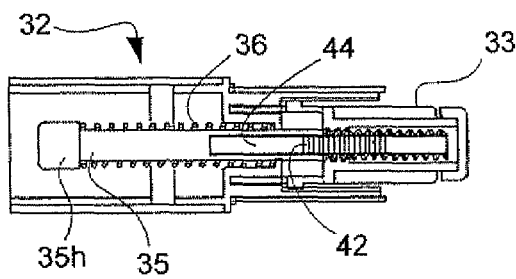
FIG. 11 is a side cross sectional view illustrating the rear casing of the injection device and the ejection volume controller member.

FIG. 10 illustrates a side cross sectional view of a front casing 31 of the injection device holding a two-compartment syringe 1 with an attached double-ended needle 18. FIG. 11 illustrates a side cross sectional view of a rear casing 32 of the injection device and other associated members such as an ejection volume controller member 33 combined with the rear casing. The numeral 35 indicates a piston rod, and 35h the head of the piston rod 35. Around the piston rod 35 is placed a coil spring 36 between the head 35h of the piston rod 35 and rear part of the rear casing 32. In rear part of the piston rod 35, a pair of racks 42 are formed on both sides of the piston rod. In the area before the racks 42, on both sides of the piston rod 35, a pair of grooves 44, of which one is visible in the figure and the other is hidden behind the piston rod 35, are defined having a bottom that is recessed relative to the top of the teeth of the racks 42. For convenience, the front casing 31 is shown with broken lines, and the piston rod 35 is shown as a side view (not as a cross sectional view). The numeral 34 indicates a pair of projections. A cantilever is formed around the foot of each projection 34 by making a U-shaped cut in the outer wall of the front casing, thereby allowing the projection 34 to resiliently retreat, though only a little.

Figure 12:
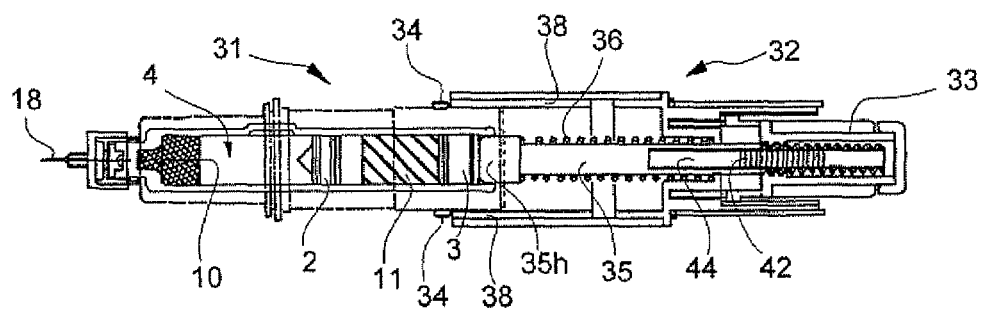
FIG. 12 is a side cross sectional view of the injection device, with part of a two-compartment syringe, held by the front casing, being inserted into the rear casing and the head of the piston rod abutting on the slidable rear wall of the two-compartment syringe.

FIG. 12 illustrates a side cross sectional view of the injection device, with part of the two-compartment syringe 1 held by the front casing 31 being inserted into the rear casing 32 and the head 35h of the piston rod 35 abutting on the slidable rear wall 3 of the two-compartment syringe 1. In the figure, the numeral 38 indicates a pair of elongated grooves defined in the inner wall of the rear casing, through which the pair of projections are to pass.

Figure 13:
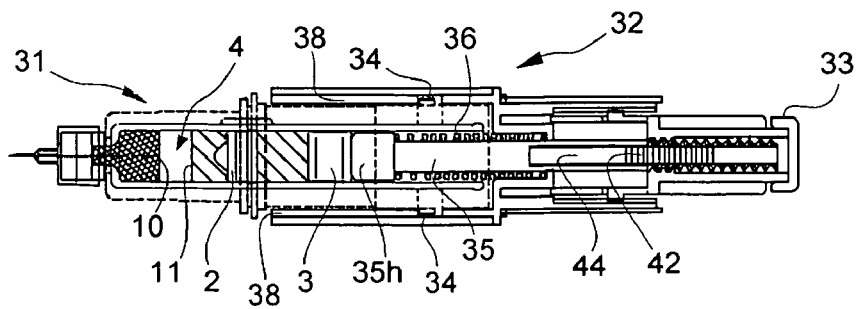
FIG. 13 is a side cross sectional view of the injection device, with the two-compartment syringe being inserted into the rear casing to its bottom.

FIG. 13 illustrates a side cross sectional view of the injection device, with the two-compartment syringe 1 having been inserted into the rear casing 32 to its bottom. In this position, the pair of projections 34 formed on the front casing 31 have just come out of the grooves 38 defined in the inner wall of the rear casing. As shown in the figure, the piston rod 35, being pressed by the slidable rear wall 3, is temporarily moved backward but is also pushing, with the repulsive force of the coil spring 36, the slidable rear wall 3 in the two-compartment syringe to make it to advance within the two-compartment syringe. As a result, the slidable rear wall 3 pushes, via and together with the solvent liquid 11, the slidable front wall 2 to drive it fully into the range of the bypass 6. Thus, the solvent liquid 11 is shown in the figure flowing into the front space 4 through the bypass 6.

Figure 14:
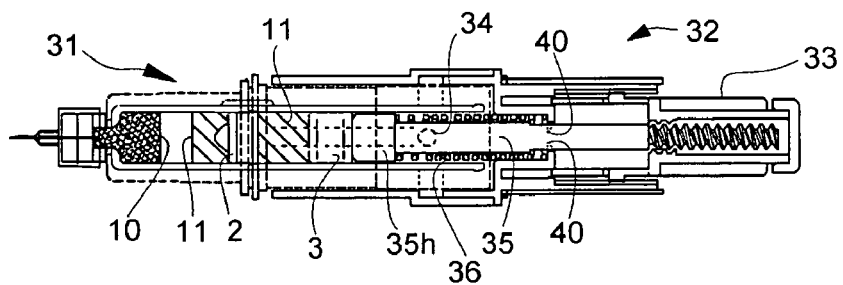
FIG. 14 is a side cross sectional view of the injection device viewed from an angle that differs by 90° from that in FIG. 13.

FIG. 14 illustrates a side cross sectional view of the injection device at the same position shown in FIG. 13, but viewed from an angle that differs by 90° from that of FIG. 13. In the figure, the numeral 40 indicates a pair of one-way stopper teeth opposed to the piston rod 35. In the position of piston rod 35 shown in FIG. 14 (the same as shown in FIG. 13), the pair of locking teeth 40 are protruding into the pair of grooves 44 in the region before the pair of the racks 42 defined in the piston rod.

Figure 15:
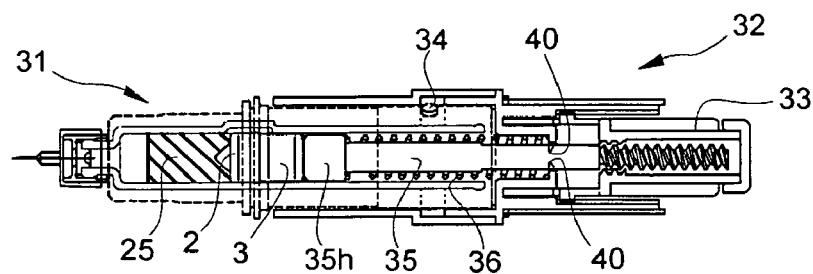
FIG. 15 is a side cross sectional view of the injection device, in which the front casing is secured to the rear casing to prevent the former from being pulled off.

FIG. 15 is a side cross sectional view showing the front casing 31 secured to the rear casing 32 to prevent the former from being pulled off, by rotating the front casing 31 relative to the rear casing 32 by about 45° from the position shown in FIG. 14 to bring a side face of each projection 43 into engagement with a face of a step formed in the inner wall surface of the rear casing 32. During this process, all the solvent liquid that was contained between the slidable rear wall 3 and the slidable front wall 2 has been transferred, by the repulsive force of the coil spring 36, into the space before the slidable front wall 2, and the dried pharmaceutical agent has thus been dissolved to give the injectable liquid 25. Atop the injectable liquid 25 is air.

Figure 16:
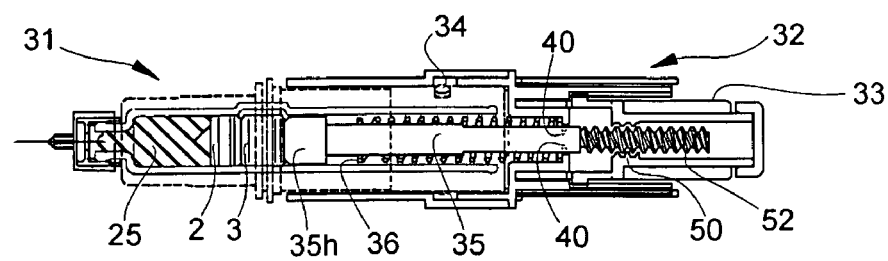
FIG. 16 is a side cross sectional view of the injection device illustrating the injection device immediately after the expulsion of air in the front end of the two-compartment syringe through the double-ended needle.

Reference is made to FIG. 16. FIG. 16, following the situation shown in FIG. 15, is a side cross sectional view illustrating the injection device immediately after the expulsion of the air in the front end of the two-compartment syringe through the double-ended needle 18, by manually pressing in the ejection volume controller member 33 against the rear casing 32. The ejection volume controller member 33 are screwed at its female screw 50 together with the male screw 52 formed on the piston rod 35. The piston rod 35 is in mutually unrotatable engagement with the rear casing, with the one-way stopper teeth 40 protruding into its grooves 44, or with the one-way stopper teeth 40 protruding between the partial male screws 52 formed on both sides of the rack 42. Therefore, a counterclockwise rotation given to the ejection volume controller member 33 will cause ejection volume controller member to retreat by a desired distance relative to the piston rod 35 and the rear casing 32. Thus, in the position shown in FIG. 15, if the ejection volume controller member 33 abuts on the rear casing 32 and therefore cannot be pressed in further, then the ejection volume controller member 33 may be rotated counterclockwise to create a gap of a desired distance between the rear casing 32 and the ejection volume controller means 33, and then be pressed in. Though not visible in the figure, in the situation shown in FIG. 16, each of the pair of one-way stopper teeth 40, after having passed through the pair of grooves 44 defined in the piston rod 35, now engages corresponding one of the pair of the racks 42. In other words, the foremost position of the rack 42 and the position of the one-way stopper teeth 40 may be determined so that the locking teeth are brought into engagement when the injectable liquid 25 has been constructed and the air in the front end expelled.

Figure 17:
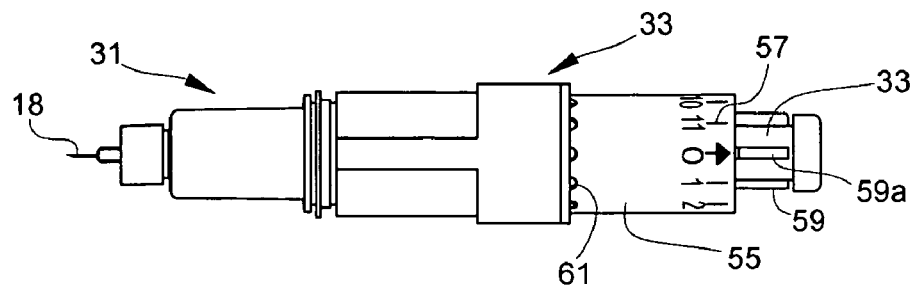
FIG. 17 is a side cross sectional view of the injection device when mixing of pharmaceutical agents has been completed.
Figure 18:
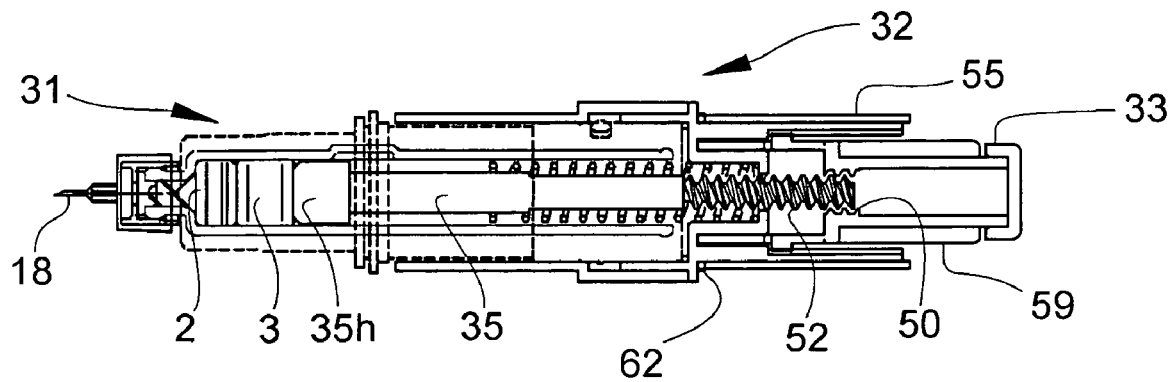
FIG. 18 is a side cross sectional view of the injection device with which the injection of all the injectable liquid has been completed.

FIG. 17 illustrates a side view of the injection device in which the mixing of the pharmaceutical agents has been completed. In the figure, the numeral 55 indicates a cylindrical sleeve that is fit to a rear portion of the rear casing 31. On the surface of the sleeve 55, multiple scale marks 57 which equally divide the circumference are given, and, at the front end, notches 61 are made which, likewise to the scale marks 57, equally divide the circumference. The notches 61, by engaging projections formed on the rear casing 32 (e.g., as those shown with the numeral 62 in FIG. 20), prevent rotation of the sleeve 55, which however, when pulled back a little, can become rotatable by hand, for it then is release from such engagement. The ejection volume controller member 33 includes, on its circumference, multiple fins oriented in the longitudinal direction. Volumes to be ejected through the double-ended needle are determined by degrees of the angle of rotation (counterclockwise with the device shown in the figure) of the ejection volume controller member 33 from its resting position where it lies abutting on the rear casing 32. In accordance with a volume to be injected into a patient, a degree of the angle of rotation of the ejection volume controller member 33 is determined, which degree of the angle is associated with one of the scale marks given on the sleeve 55. With the ejection volume controller member 33 at its resting position, a patient may, for example, by turning the sleeve to adjust its scale mark "zero" to a predetermined fin 59a and then rotating counterclockwise the ejection volume controller member 33 from the position to that associated scale mark, properly adjust the volume to be injected. Then by inserting the needle in the body and pressing the ejection volume controller member 33 until it abuts on the rear casing 32, the predetermined amount of volume is injected. The same procedure is repeated at each of the multiple injections, until the situation illustrated in FIG. 18 is finally reached, when injection of all the injectable liquid has been completed. The injection device may be disposed of when injection has been completed with all the injectable liquid in a two-compartment syringe is completed.

Figure 19:
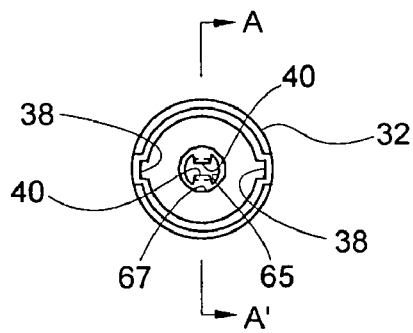
FIG. 19 is a front end elevational view of the rear casing.

FIG. 19 illustrates a frontal end elevational view of the rear casing 32. The piston rod 35 and the coil spring are omitted from the figure. As seen in the figure, an opening 65 through which the piston rod 35 runs is defined in the center of the rear casing 32, from both side of which opening inwardly protrude a pair of one-way stopper teeth 40. The numeral 67 indicates the inner surface of the cylindrical portion within which the rear end part of the coil spring 36 is received.

Figure 20:
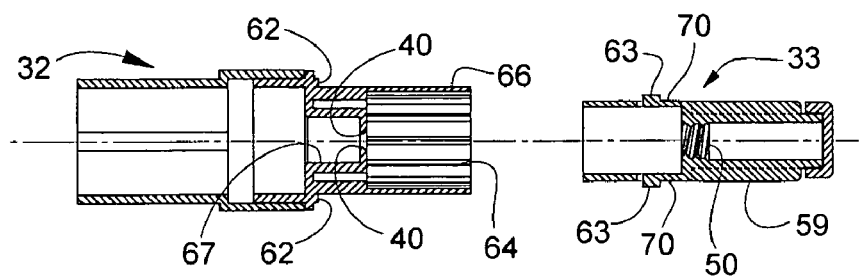
FIG. 20 is a side sectional view of the rear casing and of the ejection volume controller member.

FIG. 20 illustrates a A-A' side cross sectional view of the rear casing 32 shown in FIG. 19, with the sleeve 55 removed, as well as the ejection volume controller member 33 to be combined therewith. The ejection volume controller member 33 is inserted into the cylindrical portion 66 (over which the sleeve 55 is to be fit) formed in the rear of the rear casing 32. In the rear casing 32, each numeral 62 indicates a projection which engages each notch 61 of the sleeve 55. In the ejection volume controller member 33, each numeral 63 indicates each projection having a triangular cross section resiliently supported by a cantilever 70 formed in the outer wall of the ejection volume controller member 33, which projection engages in a snap-fit fashion with a plurality of longitudinal grooves 64 (formed at positions equally dividing the circumference as do the notches 61) having generally V-shaped cross sections defined in the inner surface of the cylindrical portion 66 of the rear casing 32. When the ejection volume controller member 33 is rotated relative to the rear casing 32, each of the projections 63 can resiliently retreat and come out of one of the longitudinal grooves with which it is in engagement, and then temporarily fix the rotational position of the ejection volume controller member 33 relative to the rear casing 32, at desired one of the angles corresponding to the position of the longitudinal groove 64. The relative positioning of the scale marks 57 on the sleeve 55, the notches 61, a predetermined fin 59a of the ejection volume controller member 33 used in adjusting to the scale marks, and the projection 63, as well as the longitudinal grooves 64 defined in the inner surface of the cylindrical portion 66 of the rear casing 32, are so configured that when a projection 63 is in engagement with some of the longitudinal grooves 64, the predetermined fin 59a meets one of the scale marks 57.

Figure 21:
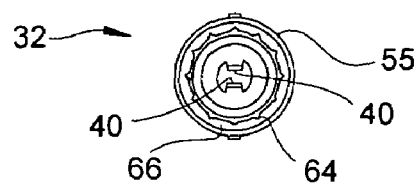
FIG. 21 is a proximal end elevational view of the rear casing.
Figure 22:
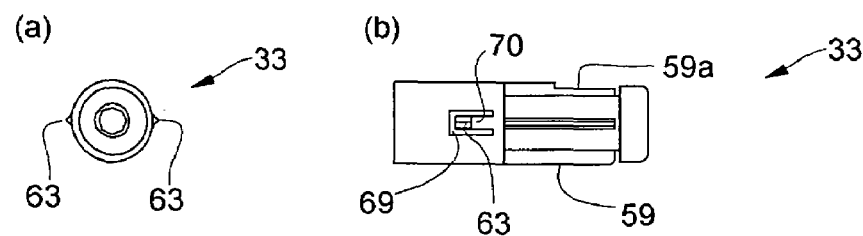
FIG. 22 is (a) a front end elevational view and (b) a side cross sectional view, of the injection volume controller member.

FIG. 21 illustrates a proximal end elevational view of the rear casing 32. Seen in the figure are the generally V-shaped transverse cross sections of the longitudinal grooves 64 defined in the cylindrical portion 66 and the number (i.e., 12) of them. The numeral 40 indicates one of the one-way stopper teeth. FIG. 22 illustrates (a) a frontal end elevational view and a side view (b) of the ejection volume controller means 33. As seen in the frontal end elevational view (a), each of the projections 63 is triangular in cross section, and, as seen in the side view (b), is formed on the resiliently deformable cantilever 70 which is surrounded by a U-shaped slit 69 made in the side wall of the ejection volume controller member 33.

Figure 23:
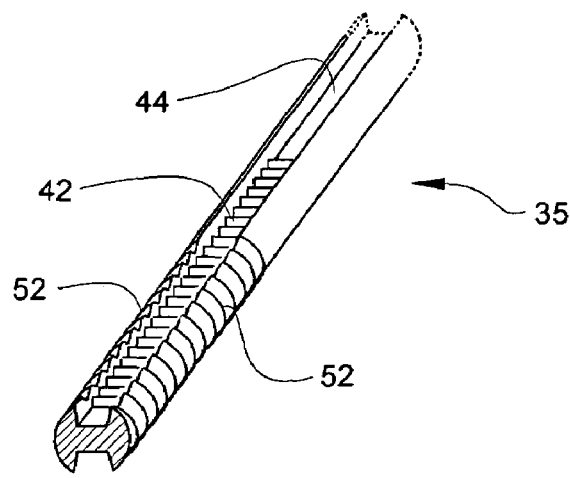
FIG. 23 is a perspective view of rear part of the piston rod, cut out and enlarged.

FIG. 23 illustrates a perspective view of a rear part of the piston rod 35, cut out and enlarged. As seen in the figure, the male screw 52 comprises a pair of partial screws provided separately and sandwiching, from both sides, rear part of the rack 42. Forward of the part in which the male screw is formed, the piston rod has partial cylindrical surfaces of the same dimensions as that of the outer circumference of the male screw 52. With this configuration, piston rod 35 can, while being in unrotatable engagement with the one-way stopper teeth 40 of the rear casing 32, be screwed with the female screw 50 of the ejection volume controller member 33, thereby allowing adjustment of ejection volume of the injectable liquid, a by being engaged in its racks by the one-way stopper teeth.

The present invention is useful in providing a disposable, low-cost injection device which guarantees a proper procedure be followed of mixing the pharmaceutical agents contained in a two-compartment syringe, and enables portion-wise multiple injections of thus constituted injectable liquid in the syringe.

What is claimed is:

1. An injection device for receiving a two-compartment syringe having a front end equipped with a septum that can be pierced by a double-ended needle, a cylindrical side wall, a slidable front wall and a slidable rear wall that are liquid-tightly and slidably fitted in the side wall, and a bypass which is defined in the internal surface of the side wall between the front end and the slidable front wall and has a longitudinal length sufficient to stride the thickness of the slidable front wall, the two-compartment syringe containing a first pharmaceutical component in the front space defined between the front end and the slidable front wall and a second, liquid pharmaceutical component in the rear space defined between the slidable front wall and the slidable rear wall; mixing, in the two-compartment syringe, the first pharmaceutical component and the second pharmaceutical component; and then conducting injection of thus prepared injectable liquid, the injection device comprising a front casing designed to enclose and hold the two-compartment syringe with a double-ended needle attached to the front end of the two-compartment syringe, a rear casing designed to receive the two-compartment syringe held by the front casing being inserted in a rear-end first manner, and to lock and hold the front casing, with the two-compartment syringe inserted in the rear casing, a piston rod placed slidably in the longitudinal direction in the rear casing and designed to push from behind and carry forward the slidable rear wall, wherein the piston rod can be pushed forwardly from behind the rear casing, and a spring provided in association with the piston rod in the region between the front end of the piston rod and rear part of the rear casing so that, when the front end of the piston rod is moved backward, the spring may be compressed and then push the piston rod to a forward position again, wherein the spring has sufficient length and strength such that, when the two-compartment syringe held by the front casing is inserted in the rear casing and the front casing is locked by the rear casing, with the septum pierced by a double-ended needle to put the front space into communication with the outside, the spring is once compressed, by the piston rod being moved backward due to the pressure applied by the slidable rear wall of the two-compartment syringe, and then, by its repulsive force, forwardly drives the slidable rear wall together with the second pharmaceutical component and the slidable front wall, and, after the rear end of the bypass is exposed behind the slidable front wall, pushing the slidable rear wall until it abuts on the slidable front wall, thereby transferring the second pharmaceutical component into the front space.

2. The injection device of claim 1 further comprising a one-way stopper means which, at a position forward of the position where the piston rod rests before insertion of the two-compartment syringe, allows the piston rod to be pressed in and advanced but prevents the piston rod from being moved backward.

3. The injection device of claim 2, wherein the one-way stopper means comprises a rack formed on the piston rod and a one-way stopper tooth that is formed in the rear casing and engages the rack to prevent backward movement of the rack.

4. The injection device of claim 3, wherein the rack is formed on the piston rod in the rear of the position of the piston rod that comes opposite to the one-way stopper tooth when the piston rod is supported, before the insertion of the two-compartment syringe, by the spring at the natural length thereof.

5. The injection device of claim 4, wherein the piston rod is in mutually unrotatable engagement with the rear casing, wherein behind the rear casing is provided, in a rotatable fashion relative to the rear casing, an ejection volume controller member having a female screw through which the piston rod runs, and wherein, on the outer surface of the piston rod, a male screw is formed which engages the female screw.

6. The injection device of claim 5, wherein the piston rod and the rear casing are made mutually unrotatable by having non-circular cross sections that engage with each other.

7. The injection device of claim 6, wherein the piston rod and the rear casing is made mutually unrotatable through engagement of the piston rod and the one-way stopper tooth of the rear casing.

8. The injection device of claim 5, wherein the male screw is a partial screw formed so as to sandwich the rack from both sides thereof.

9. The injection device of claim 8, wherein the rack has teeth with tops and the threads of the male screw on both sides of the rack project higher than the tops of the teeth of the rack.

10. An injection device for receiving a two-compartment syringe having a front end equipped with a septum that can he pierced by a double-ended needle, a cylindrical side wall, a slidable front wall and a slidable rear wall that are liquid-tightly and slidably fitted in the side wall, and a bypass which is defined in the internal surface of the side wall between the front end and the slidable front wall and has a longitudinal length sufficient to stride the thickness of the slidable front wall, the two-compartment syringe containing a first pharmaceutical component in the front space defined between the front end and the slidable front wall and a second, liquid pharmaceutical component in the rear space defined between the slidable front wall and the slidable rear wall; mixing, in the two-compartment syringe, the first pharmaceutical component and the second pharmaceutical component; and then conducting injection of thus prepared injectable liquid, the injection device comprising a front casing designed to enclose and hold the two-compartment syringe with a double-ended needle attached to the front end of the two-compartment syringe, a rear casing designed to receive the two-compartment syringe held by the front casing being inserted in a rear-end first manner, and to lock and hold the front casing, with the two-compartment syringe inserted in the rear casing, a piston rod placed slidably in the longitudinal direction in the rear casing and designed to engage, push from behind and carry forward the slidable rear wall, wherein the piston rod can be pushed forwardly from behind the rear casing, and a spring provided in association with the piston rod in the region between the front end of the piston rod and rear part of the rear casing, the spring being initially uncompressed so that when the front end of the piston rod is moved backward, the spring is compressed and biases the piston rod to a forward position again, wherein the spring has sufficient length and strength when uncompressed, such that when the two-compartment syringe held by the front casing is inserted in the rear casing, the spring is compressed by engagement between the front end of the piston rod and the slidable rear wall, and the front casing is locked by respective movement into the rear easing while the septum is pierced by a double-ended needle to put the front space into communication with the outside; wherein while the spring is being compressed in the injection device by the piston rod being moved backward due to the pressure applied by the slidable rear wall of the two-compartment syringe, the spring by its repulsive force forwardly drives the slidable rear wall together with the second pharmaceutical component and the slidable front wall, and after the rear end of the bypass is exposed behind the slidable front wall, pushes the slidable rear wall until it abuts on the slidable front wall, thereby transferring the second pharmaceutical component into the front space to mix with the first pharmaceutical component.

* * * * *